US00PP07850P

United States Patent [19]

VandenBerg

[11] Patent Number: Plant 7,850

[45] Date of Patent: Mar. 31, 1992

[54] CHRYSANTHEMUM PLANT NAMED CHERRY POMONA

[75] Inventor: Cornelis P. VandenBerg, Salinas, Calif.

[73] Assignee: Yoder Brothers, Inc., Barberton, Ohio

[21] Appl. No.: 571,404

[22] Filed: Aug. 23, 1990

[51] Int. Cl.[5] ..... A01H 5/00

[52] U.S. Cl. ..... Plt./82

[58] Field of Search ..... Plt./76, 80, 81, 82

[56] References Cited

U.S. PATENT DOCUMENTS

P.P. 6,802 5/1989 VandenBerg ..... Plt. 80

4,616,099 10/1986 Sparkes ..... 47/58

OTHER PUBLICATIONS

Broertjes et al., A Mutant of a Mutant of a Mutant of a . . . Irradiation of Progressive Radiation-Induced Mutants in a Mutation-Breeding Programme with *Chrysanthemum morifolium,* Euphytica (29):525-530.

Broertjes et al., 1978, "*Application of Mutation Breeding Methods in the Improvement of Vegetatively Propagated Crops*", Elsevier Sci. Pub. Co., New York, pp. 162-175.

Broertjes, 1966, Mutation Breeding of Chrysanthemums, Euphytica (15) 156-162.

Searle, et al., 1968, "*Chrysanthemums the Year Round*", Blandford Press, Ltd., London, England, pp. 27-29, 321-327.

Gosling, ed., 1979, "*The Chrysanthemum Manual*", of the National Chrysanthemum Society, Essex Telegraph Ltd., Colchester, England, pp. 329-336.

Chan. 1966, Chrysanthemum and Rose Mutations Induced by X-Rays, Am. Soc. Hort. Sci., vol. 88, pp. 613-620.

Dowrick et al., 1966, The Induction of Mutations in Chrysanthemums Using X- and Gamma Radiation, Euphytica (15):204-210.

*Primary Examiner*—Howard J. Locker

*Attorney, Agent, or Firm*—Foley & Lardner

[57] ABSTRACT

A Chrysanthemum plant named Cherry Pomona particularly characterized by its flat capitulum form; decorative capitulum type; cherry red ray floret color; diameter across face of capitulum of 125 to 135 mm. when fully opened when grown as a pinched disbudded pot mum; photoperiodic response to short days of 51 to 56 days; plant height of 20 to 30 cm. when grown as a pinched pot mum; recommended both as disbudded and spray pot mum; and spreading and prolific branching pattern, with 5 to 6 breaks per plant after pinch.

1 Drawing Sheet

The present invention comprises a new and distinct cultivar of Chrysanthemum, botanically known as *Dendranthema grandiflora,* and referred to by the cultivar name Cherry Pomona.

Cherry Pomona, identified as 81-893G19, is a product of a mutation induction program which had the objective of creating new Chrysanthemum cultivars that would expand the color range of an existing cultivar while retaining all other traits.

Cherry Pomona was discovered and selected by Cornelis P. VandenBerg in May 1987 in a controlled environment in Salinas, Calif. as one flowering plant within a flowering block established as rooted cuttings from stock plants which had been exposed as unrooted cuttings to an X-ray source of 2000 rads. The irradiated parent was the cultivar identified as Pomona, disclosed in U.S. Plant Pat. No. 6,802.

The first act of asexual reproduction of Cherry Pomona was accomplished when vegetative cuttings were taken from the initial selection in July 1987 in a controlled environment in Salinas, Calif., by technicians working under the supervision of Cornelis P. VandenBerg.

Horticultural examination of controlled flowerings of successive plantings has shown that the unique combination of characteristics as herein disclosed for Cherry Pomona are firmly fixed and are retained through successive generations of asexual reproduction.

Cherry Pomona has not been observed under all possible environmental conditions. The phenotype may vary significantly with variations in environment such as temperature, light intensity and daylength.

The following observations, measurements and comparisons describe plants grown in Salinas, Calif. under greenhouse conditions which approxmate those generally used in commercial greenhouse practice.

The following traits have been repeatedly observed and are determined to be basic characteristics of Cherry Pomona, which, in combination, distinguish this Chrysanthemum as a new and distinct cultivar:

1. Flat capitulum form.
2. Decorative capitulum type.
3. Cherry red ray floret color.
4. Diameter across face of capitulum of 125 to 135 mm. when fully opened, when grown as a pinched disbudded pot mum.
5. Photoperiodic flowering response to short days of 51 to 56 days.
6. Plant height, with 15 long days after sticking unrooted cuttings, and with 1 to 3 applications of 2500 ppm B-9 SP, ranges from 20 to 30 cm. when grown as a pinched pot mum with 4 cuttings in a 15 cm. pot.
7. Recommended both as disbudded and spray pot mum.
8. Branching pattern is spreading and prolific, each plant having 5 to 6 laterals after pinch.

The accompanying photographic drawing is a color photograph of Cherry Pomona grown as a pinched spray pot mum with 4 cuttings in a 15 cm. pot.

Of the commercial cultivars known to the inventor, the most similar in comparison to Cherry Pomona is the parent cultivar Pomona. All traits of Cherry Pomona are similar to those of Pomona, except the color of ray florets. Cherry Pomona has a cherry red ray floret color, while the color of Pomona is red-purple.

In the following description color references are made to The Royal Horticultural Society Colour Chart. The actual color of Cherry Pomona is not represented in The R.H.S. Colour Chart, and the values given are those believed to be closest to the actual color of Cherry Pomona. The color values were determined on plant material grown as a pinched spray pot mum in Salinas, Calif. on May 8, 1990.

Classification:

*Botanical.*—*Dendranthema grandiflora* cv Cherry Pomona.

*Commercial.*—Decorative disbud and spray pot mum.

INFLORESCENCE

A. Capitulum:

*Form.*—Flat.

*Type.*—Decorative.

*Diameter across face.*—125 to 135 mm. when fully opened.

B. Corolla of ray florets:

*Color (general tonality from a distance of three meters).*—Cherry red.

*Color.*—Upper surface: 181A to 181B, fading to 181C. Under surface: 182D, slightly streaked with 181C.

*Shape.*—Flat, oblong.

C. Corolla of disc florets:

*Color (mature).*—14B.

*Color (immature).*—14B, overlaid with 144B.

D. Reproductive organs:

*Androecium.*—Present on disc florets only; very few disc florets; moderate pollen.

*Gynoecium.*—Present on both ray and disc florets.

PLANT

A. General appearance:

*Height.*—20 to 30 cm. when grown as a pinched pot mum in a 15 cm. pot with 15 long days after direct sticking of unrooted cuttings and 1 to 3 applications of 2500 ppm B-9 SP.

*Branching pattern.*—Spreading and prolific, with 5 to 6 laterals after pinch.

B. Foliage:

*Color (upper surface).*—147A.

*Color (under surface).*—147B.

*Shape.*—Lobed and slightly serrated (see photograph).

I claim:

1. A new and distinct Chrysanthemum plant named Cherry Pomona, as described and illustrated.

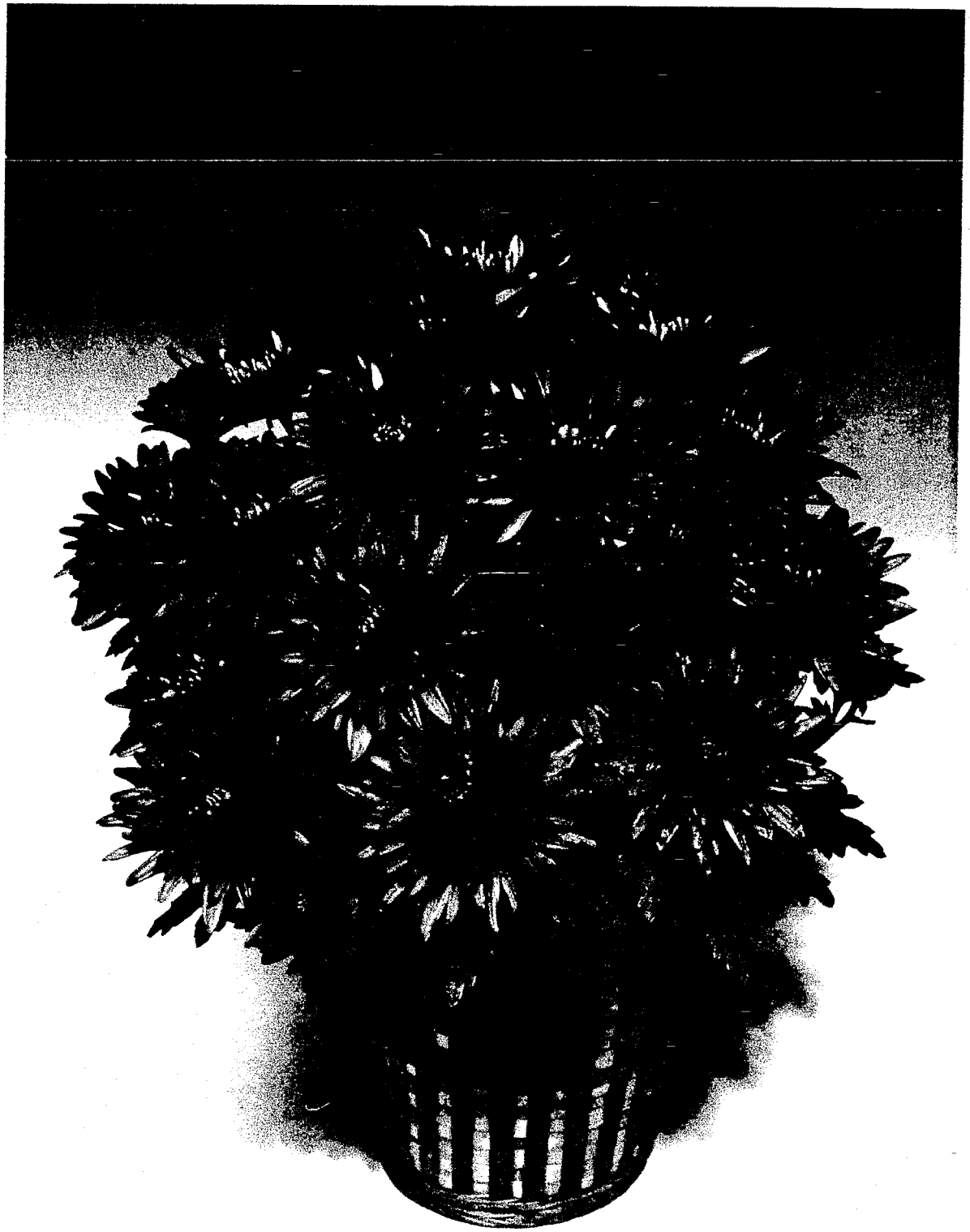

* * * * *